United States Patent
Schuele et al.

(10) Patent No.: US 10,888,459 B2
(45) Date of Patent: Jan. 12, 2021

(54) MICROFEMTOTOMY METHODS AND SYSTEMS

(71) Applicant: OPTIMEDICA CORPORATION, Santa Ana, CA (US)

(72) Inventors: Georg Schuele, Menlo Park, CA (US); Julian Stevens, London (GB); Dan E. Andersen, Menlo Park, CA (US)

(73) Assignee: AMO Development, LLC, Santa Ana, CA (US)

( * ) Notice: Subject to any disclaimer, the term of this patent is extended or adjusted under 35 U.S.C. 154(b) by 257 days.

(21) Appl. No.: 15/952,147

(22) Filed: Apr. 12, 2018

(65) Prior Publication Data
US 2018/0296392 A1   Oct. 18, 2018

Related U.S. Application Data

(62) Division of application No. 14/199,087, filed on Mar. 6, 2014, now abandoned.
(Continued)

(51) Int. Cl.
*A61F 9/007* (2006.01)
*A61F 9/00* (2006.01)
(Continued)

(52) U.S. Cl.
CPC ........ *A61F 9/00754* (2013.01); *A61F 9/0017* (2013.01); *A61F 9/00834* (2013.01);
(Continued)

(58) Field of Classification Search
CPC .............. A61F 9/0017; A61F 9/00754; A61F 9/00831; A61F 2009/0087; A61F 2009/00889
(Continued)

(56) References Cited

U.S. PATENT DOCUMENTS

| 5,459,570 A | 10/1995 | Swanson et al. |
| 5,720,894 A | 2/1998 | Neev et al. |

(Continued)

FOREIGN PATENT DOCUMENTS

| EP | 2422746 A1 | 2/2012 |
| EP | 2422747 A1 | 2/2012 |

(Continued)

OTHER PUBLICATIONS

International Search Report and Written Opinion for Application No. PCT/US2014/021119, dated Jul. 15, 2014, 16 pages.

*Primary Examiner* — Nathan J Jenness
(74) *Attorney, Agent, or Firm* — Johnson & Johnson Surgical Vision, Inc.

(57) ABSTRACT

Methods and systems for performing laser-assisted surgery on an eye form one or more small anchoring capsulotomies in the lens capsule of the eye. The one or more anchoring capsulotomies are configured to accommodate corresponding anchoring features of an intraocular lens and/or to accommodate one or more drug-eluting members. A method for performing laser-assisted eye surgery on an eye having a lens capsule includes forming an anchoring capsulotomy in the lens capsule and coupling an anchoring feature of the intraocular lens with the anchoring capsulotomy. The anchoring capsulotomy is formed by using a laser to incise the lens capsule. The anchoring feature can protrude transverse to a surface of the intraocular lens that interfaces with the lens capsule adjacent to the anchoring capsulotomy.

9 Claims, 10 Drawing Sheets

Related U.S. Application Data

(60) Provisional application No. 61/788,201, filed on Mar. 15, 2013.

(51) Int. Cl.
    *A61F 9/008*     (2006.01)
    *A61F 2/16*     (2006.01)

(52) U.S. Cl.
    CPC ......... *A61F 2/16* (2013.01); *A61F 2009/0087* (2013.01); *A61F 2009/00851* (2013.01); *A61F 2009/00889* (2013.01)

(58) Field of Classification Search
    USPC ........ 606/4–6; 623/6.34–6.55; 424/427–428; 604/294–302
    See application file for complete search history.

(56) References Cited

U.S. PATENT DOCUMENTS

| | | |
|---|---|---|
| 5,722,970 A | 3/1998 | Colvard et al. |
| 5,748,352 A | 5/1998 | Hattori |
| 5,748,898 A | 5/1998 | Ueda |
| 5,957,915 A | 9/1999 | Trost |
| 5,984,916 A | 11/1999 | Lai |
| 6,019,472 A | 2/2000 | Koester et al. |
| 6,053,613 A | 4/2000 | Wei et al. |
| 6,111,645 A | 8/2000 | Tearney et al. |
| 6,454,761 B1 | 9/2002 | Freedman |
| 6,719,750 B2 * | 4/2004 | Varner .................. A61P 27/02 604/289 |
| 7,655,002 B2 | 2/2010 | Myers et al. |
| 7,717,907 B2 | 5/2010 | Ruiz et al. |
| 8,262,646 B2 | 9/2012 | Frey et al. |
| 8,350,183 B2 | 1/2013 | Vogel et al. |
| 8,382,745 B2 | 2/2013 | Naranjo-Tackman et al. |
| 8,414,564 B2 | 4/2013 | Goldshleger et al. |
| 2003/0036796 A1 | 2/2003 | Laguette et al. |
| 2004/0010284 A1 | 1/2004 | Maloof et al. |
| 2004/0098122 A1 | 5/2004 | Lee et al. |
| 2006/0195076 A1 | 8/2006 | Blumenkranz et al. |
| 2008/0103592 A1 | 5/2008 | Maloney |
| 2008/0281413 A1 | 11/2008 | Culbertson et al. |
| 2009/0222087 A1 * | 9/2009 | Coroneo .................. A61F 2/16 623/6.43 |
| 2010/0022995 A1 | 1/2010 | Frey et al. |
| 2010/0121444 A1 | 5/2010 | Ben |
| 2010/0233071 A1 | 9/2010 | Fukai |
| 2011/0172649 A1 | 7/2011 | Schuele |
| 2011/0202046 A1 | 8/2011 | Angeley et al. |
| 2011/0251686 A1 | 10/2011 | Masket |
| 2011/0319873 A1 | 12/2011 | Raksi et al. |
| 2011/0319875 A1 | 12/2011 | Loesel et al. |
| 2012/0078362 A1 * | 3/2012 | Haffner ............... A61F 9/00781 623/6.13 |
| 2013/0331937 A1 | 12/2013 | Stevens |

FOREIGN PATENT DOCUMENTS

| | | |
|---|---|---|
| JP | 2002360616 A | 12/2002 |
| JP | 2012091053 A | 5/2012 |
| WO | 2008112292 A1 | 9/2008 |

\* cited by examiner

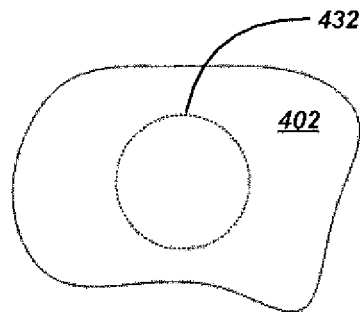
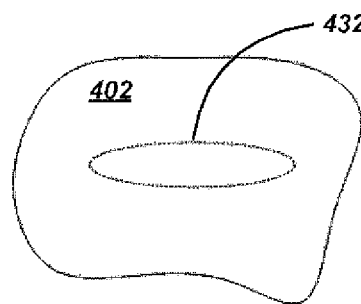
Figure 7A     Figure 7B
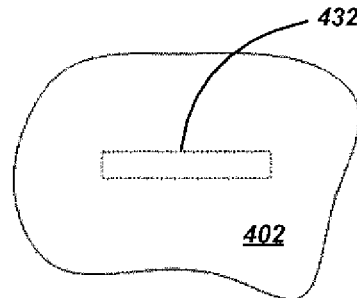
Figure 7C
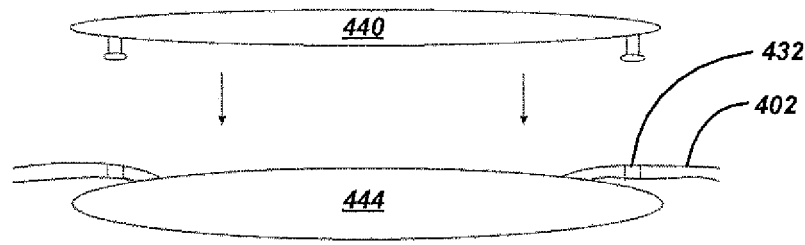
Figure 8A
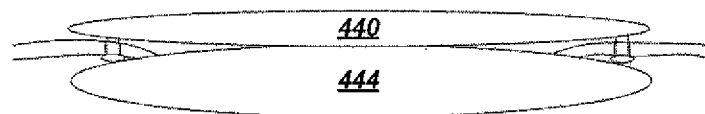
Figure 8B

MICROFEMTOMY METHODS AND SYSTEMS

CROSS-REFERENCES TO RELATED APPLICATIONS

This application is a divisional of U.S. Pat. Appl. No. 14/199,087, filed Mar. 6, 2014, which claims priority to U.S. provisional application No. 61/788,201 filed on Mar. 15, 2013. The entire contents of the above-referenced applications are incorporated herein by reference.

BACKGROUND

Cataract extraction is one of the most commonly performed surgical procedures in the world. A cataract is formed by opacification of the crystalline lens or its envelope—the lens capsule—of the eye. The cataract obstructs passage of light through the lens. A cataract can vary in degree from slight to complete opacity. Early in the development of an age-related cataract the power of the lens may be increased, causing near-sightedness (myopia). Gradual yellowing and opacification of the lens may reduce the perception of blue colors as those wavelengths are absorbed and scattered within the crystalline lens. Cataract formation typically progresses slowly resulting in progressive vision loss. Cataracts are potentially blinding if untreated.

A common cataract treatment involves replacing the opaque crystalline lens with an artificial intraocular lens (IOL). Presently, an estimated 15 million cataract surgeries per year are performed worldwide. The cataract treatment market is composed of various segments including intraocular lenses for implantation, viscoelastic polymers to facilitate surgical maneuvers, and disposable instrumentation including ultrasonic phacoemulsification tips, tubing, various knives, and forceps.

Presently, cataract surgery is typically performed using a technique termed phacoemulsification in which an ultrasonic tip with associated irrigation and aspiration ports is used to sculpt the relatively hard nucleus of the lens to facilitate removal through an opening made in the anterior lens capsule. The nucleus of the lens is contained within an outer membrane of the lens that is referred to as the lens capsule. Access to the lens nucleus can be provided by performing an anterior capsulotomy in which a small round hole is formed in the anterior side of the lens capsule. Access to the lens nucleus can also be provided by performing a manual continuous curvilinear capsulorhexis (CCC) procedure. After removal of the lens nucleus, a synthetic foldable intraocular lens (IOL) can be inserted into the remaining lens capsule of the eye through a small incision. Typically, the IOL is held in place by the edges of the anterior capsule and the capsular bag. The IOL may also be held by the posterior capsule, either alone or in unison with the anterior capsule. This latter configuration is known in the field as a "Bag-in-Lens" implant.

One of the most technically challenging and critical steps in the cataract extraction procedure is providing access to the lens nucleus. The manual continuous curvilinear capsulorhexis (CCC) procedure evolved from an earlier technique termed can-opener capsulotomy in which a sharp needle was used to perforate the anterior lens capsule in a circular fashion followed by the removal of a circular fragment of lens capsule typically in the range of 5-8 mm in diameter. The smaller the capsulotomy, the more difficult it is to produce manually. The capsulotomy facilitates the next step of nuclear sculpting by phacoemulsification. Due to a variety of complications associated with the initial can-opener technique, attempts were made by leading experts in the field to develop a better technique for removal of the anterior lens capsule preceding the emulsification step.

The desired outcome of the manual continuous curvilinear capsulorhexis is to provide a smooth continuous circular opening through which not only the phacoemulsification of the nucleus can be performed safely and easily, but also to provide for easy insertion of the intraocular lens. The resulting opening in the anterior capsule provides both a clear central access for tool insertion during removal of the nucleus and for IOL insertion, a permanent aperture for transmission of the image to the retina of the patient, and also support of the IOL inside the remaining capsule that limits the potential for dislocation. The resulting reliance on the shape, symmetry, uniformity, and strength of the remaining capsule to contain, constrain, position, and maintain the IOL in the patient's eye limits the placement accuracy of the IOL, both initially and over time. Subsequently, a patient's refractive outcome and resultant visual acuity are less deterministic and intrinsically sub-optimal due to the IOL placement uncertainty. This is especially true for astigmatism correcting ("toric") and accommodating ("presbyopic") IOLs.

Problems may also develop related to inability of the surgeon to adequately visualize the capsule due to lack of red reflex, to grasp the capsule with sufficient security, and to tear a smooth circular opening in the capsule of the appropriate size and in the correct location without creating radial rips and extensions. Also present are technical difficulties related to maintenance of the depth of the anterior chamber depth after opening the capsule, small size of the pupil, or the absence of a red reflex due to the lens opacity. Some of the problems with visualization can be minimized through the use of dyes such as methylene blue or indocyanine green. Additional complications may also arise in patients with weak zonules (typically older patients) and very young children that have very soft and elastic capsules, which are very difficult to controllably and reliably rupture and tear.

The implantation of a "Bag-in-Lens" IOL typically uses anterior and posterior openings in the lens capsule of the same size. Manually creating matching anterior and posterior capsulotomies for the "Bag-in-Lens" configuration, however, is particularly difficult.

Many cataract patients have astigmatic visual errors. Astigmatism can occur when the corneal curvature is unequal in all directions. IOLs can be used to correct for astigmatism but require precise rotational and central placement. Additionally, IOLs are not typically used for correction beyond 5D of astigmatism. Many patients, however, have astigmatic visual errors exceeding 5D. Higher correction beyond 5D typically requires reshaping the cornea to make it more spherical. There are numerous existing approaches for reshaping the cornea, including Corneaplasty, Astigmatic Keratotomy, Corneal Relaxing Incision (CRI), and Limbal Relaxing Incision (LRI). In Astigmatic Keratotomy, Corneal Relaxing Incision (CRI), and Limbal Relaxing Incision (LRI), corneal incisions are made in a well-defined manner and depth to allow the cornea to change shape to become more spherical. Presently, these corneal incisions are typically accomplished manually often with limited precision.

There are also many ongoing ophthalmic needs that are less than ideally addressed by the prior methods for time-release of a drug.

Thus, improved methods and systems for treating eyes are needed.

SUMMARY

Methods and apparatus are provided for the creation of either one or more anchoring capsulotomies, which may comprise microfemtotomies. The anchoring capsulotomies such as comprise microfemtotomies can engage with complementary anchoring features on an intraocular lens for intracapsular, anterior, and/or posterior chamber placement. The anchoring capsulotomies and/or microfemtotomies can also be used to anchor capsular fixated drug-eluting implants.

Although specific reference is made to the removal and treatment of a cataract, the methods and apparatus as described herein can be used with one or more of many surgical procedures, for example anchoring incisions of a non-cataractous eye of a patient.

In many embodiments, a pattern of anchoring capsulotomies is created in a lens capsule of an eye and an intraocular lens (IOL) is then coupled to the lens capsule by mechanically engaging anchoring features of the IOL to the pattern of anchoring capsulotomies. The IOL may comprise an non-accommodating IOL or an accommodating IOL. And in many embodiments, an axial orientation to be established between the TOL and the lens capsule is determined. The eye may comprise a rotational axis, and the pattern can be located so as to align an axis the IOL or other implant with an intended axis of the eye. In many embodiments, the IOL may comprise an aberration correction, for example astigmatism or other aberration along an axis such as a higher order aberration, and the pattern of anchoring features can be placed on the eye at locations that align the axis of the IOL or other implant with the axis of the eye. In many embodiments, an axis of an astigmatic correction is determined, and the pattern rotated on the eye to locate the small capsulotomies to receive features of the IOL such that the IOL is placed at a vision correcting axis and rotation of the IOL away from the axis is inhibited when placed. Alternatively or in combination, the small capsulotomies can be located so as to align a center of the IOL with the optical axis of the eye. In many embodiments, a processor comprises a computer readable medium having instructions embodied thereon to determine angular locations of the small capsulotomies on the eye in order to align an axis of the IOL or other implant with the axis of the eye. In many embodiments, the anchoring features comprise a pre-determined angular orientation with respect to the aberration correcting axis of the IOL, and the small capsulotomies are located to align the aberration correcting axis of the IOL with the aberration axis of the eye.

The anchoring capsulotomies can be located to accomplish the determined axial orientation upon assembly or unrolling of the IOL with the lens capsule. Accordingly, an IOL can be held in a desired position and orientation relative to the lens capsule, thereby avoiding undesirable aspects related to having an TOL shift position and/or orientation relative to the lens capsule. The IOL can also be located in different locations within the eye including, but not limited to, in an anterior chamber of the eye, in a capsular bag of the eye, on the anterior side of a posterior capsule of the eye, or on the posterior side of an anterior capsule of the eye. Such flexibility in the location of the IOL within the eye provides increased treatment flexibility, such as the ability to install a second IOL anteriorly to an IOL that was previously implanted.

In one aspect, a method of ophthalmic intervention is provided. The method includes creating a pattern of anchoring capsulotomies in a lens capsule of an eye. The pattern of anchoring capsulotomies is configured to be mechanically coupled to anchoring features of an intraocular lens (IOL). The IOL is then coupled to the lens capsule by mechanically engaging the anchoring features of the IOL with the pattern of anchoring capsulotomies In another aspect, "micro-femtotomies", or small capsulotomies, are formed in the lens capsule to position and orient an IOL. The TOL can even be "piggybacked" above an existing IOL. Piggybacking an IOL above an existing TOL may be desired when an optical adjustment is required and it is desired to avoid the intrusiveness and risks of removing the original IOL. Such an optical adjustment may be required as a result of, for example, the growth of a child's eyes, etc. If the original TOL is seated well, but not in the right place, a well positioned piggyback IOL can be used to balance the patient's optical system. The overlaying IOL can provide cylindrical/toric optical corrections, can be made thicker in one region and thinner in another, or can utilize refractive index profiles for aberration control.

The small capsulotomies can be made using a variety of shapes. Non-radially symmetric shapes such as lines, rectangles, squares, and ellipses can be used to complement features on the device to be implanted in order to hold the features.

In many embodiments, methods and apparatus are provided for improved delivery of therapeutic agents such as drugs. Non-limiting examples of applications for the methods disclosed herein for time-release of a drug include glaucoma medications, anti-vascular endothelial growth factor (VEGF) treatments, and the release of therapeutic agents such as diclofenac sodium, ketorolac tromethamine, and cytotoxic LEC-specific genes to combat PCO. Additional non-limiting examples include other compounds that improve the chemical diffusion or pumping of the cornea. Typical time-release drug placement is achieved by means of their injection into a surgically produced pocket within the eye, which provides a comparatively unstable platform. In contrast, an improved approach is provided that does not involve sutures or other physical restraints. In an embodiment, a microfemtotomy is used to support a drug-eluting device or pellet.

The creation of such small capsulotomies, especially with smoothly rounded edges, is practically impossible to perform manually. Additionally, plasma-mediated (or photo disruptive) capsulotomies are actually stronger than manually created capsulorhexses. This is a surprising result because there is a bounty of medical and scientific literature reporting that attempts to use energy-driven devices for capsulotomy have always yielded inferior incision edge strength when compared to manual capsulorhexsis. The increased strength of plasma-mediated capsulotomies further enhances the importance of the present inventive approach to the creation of microfemtotomy, or small laser-created capsulotomy.

BRIEF DESCRIPTION OF THE DRAWINGS

A better understanding of the features and advantages of the present disclosure will be obtained by reference to the following detailed description that sets forth illustrative embodiments, in which the principles of the disclosure are utilized, and the accompanying drawings of which:

FIGS. 7A through 7C show example anchoring capsulotomy shapes, including buttonhole incisions, in accordance with many embodiments;

FIGS. 8A and 8B show an IOL being implanted over an existing lens using anchoring capsulotomies, in accordance with an embodiment, in accordance with many embodiments;

DETAILED DESCRIPTION

In the following description, various embodiments of the present disclosure will be described. For purposes of explanation, specific configurations and details are set forth in order to provide a thorough understanding of the embodiments. However, it will also be apparent to one skilled in the art that the present disclosure may be practiced without the specific details. Furthermore, well-known features may be omitted or simplified in order not to obscure the embodiment being described.

Methods and systems for performing laser-assisted eye surgery are provided in which one or more small anchoring capsulotomies are formed in the lens capsule of an eye. The one or more anchoring capsulotomies can be used to accommodate one or more corresponding anchoring features of an intraocular lens (IOL), thereby restraining the IOL relative to the lens capsule. An anchoring capsulotomy can also be used to accommodate a drug-eluting member to deliver a therapeutic agent over time. The anchoring capsulotomies can also be used to restrain and orient a "piggy back" IOL anterior to an existing optical structure (e.g., a first IOL, a natural lens) that is restrained by the lens capsule.

Figure 1:
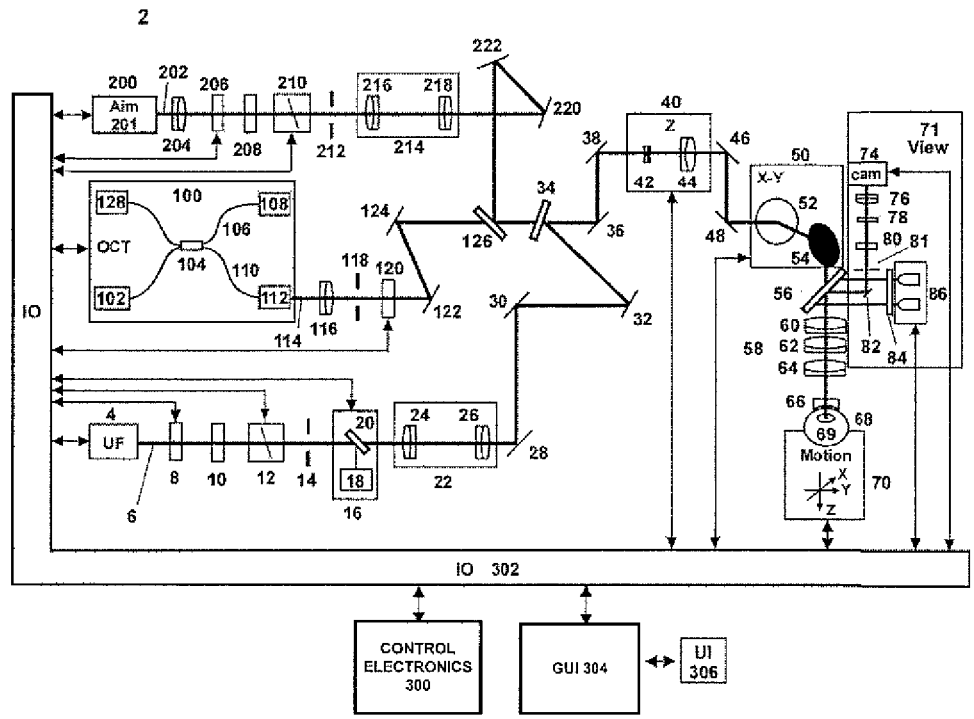
FIG. 1 shows a schematic representation of an embodiment of a system capable of creating anchoring capsulotomies, in accordance with many embodiments.

The methods disclosed herein can be implemented by a system that projects or scans an optical beam into a patient's eye 68, such as system 2 shown in FIG. 1. System 2 includes an ultrafast (UF) light source 4 (e.g., a femtosecond laser). Using system 2, a beam can be scanned in the patient's eye 68 in three dimensions: X, Y, Z. Short-pulsed laser light can be focused into eye tissue to produce dielectric breakdown to cause photo disruption around the focal point (the focal zone), thereby rupturing the tissue in the vicinity of the photo-induced plasma. In this embodiment, the wavelength of the laser light can vary between 800 nm to 1200 nm and the pulse width of the laser light can vary from 10 fs to 10000 fs. The pulse repetition frequency can also vary from 10 kHz to 500 kHz. Safety limits with regard to unintended damage to non-targeted tissue bound the upper limit with regard to repetition rate and pulse energy. And threshold energy, time to complete the procedure, and stability bound the lower limit for pulse energy and repetition rate. The peak power of the focused spot in the eye 68 and specifically within the crystalline lens 69 and anterior capsule of the eye is sufficient to produce optical breakdown and initiate a plasma-mediated ablation process. Although near-infrared wavelengths are used in many embodiments because linear optical absorption and scattering in biological tissue is reduced for near-infrared wavelengths, many alternative embodiments comprise one or more of visible, ultraviolet or infrared light energy. As a non-limiting example, laser 4 can be a repetitively pulsed 1035 nm device that produces 500 fs pulses at a repetition rate of 100 kHz and individual pulse energy in the 1 to 20 micro joule range. In general, any suitable laser having any suitable parameters can be used. An example of such a suitable system is described U.S. patent application Ser. No. 11/328,970, in the name of Blumenkranz et al., entitled "METHOD AND APPARATUS FOR PATTERNED PLASMA-MEDIATED LASR TREPHENATION OF THE LENS AND CAPSULE IN THREE DIMENSOINAL PHACO-SEGMENTATION", Pub. No. 2006/0195076, the entire disclosure of which is incorporated herein by reference. Embodiments of an ultraviolet laser suitable for combination in accordance with embodiments described herein are described in U.S. patent application Ser. No. 12/987,069, in the name of Schuele et al., entitled, "METHOD AND SYSTEM FOR MODIFYING EYE TISSUE AND INTRAOCULAR LENSES", Pub. No. 2011/0172649, the entire disclosure of which is incorporated herein by reference.

The laser 4 is controlled by control electronics 300, via an input and output device 302, to create optical beam 6. Control electronics 300 may comprise a processor such as a computer, microcontroller, etc. In this example, the controller 300 controls the entire system and data is moved through input/output device IO 302. A graphical user interface GUI 304 can be used to set system operating parameters, process user input (UI) 306, and display gathered information such as images of ocular structures. The GUI 304 and UI 306 may comprise components of a known computer system, for example one or more of a display, a touch screen display, keyboard, a pointer or a mouse, for example. The control electronics may comprise one or more processors of a computer system, for example.

The control electronics 300 can be configured in one or more of many ways, and may comprise a processor having a tangible medium having instructions of a computer program embodied thereon. In many embodiments, the tangible medium comprises a computer readable memory having instructions of a computer readable medium embodied thereon. Alternatively or in combination, the control electronic may comprise array logic such as a gate array, a programmable gate array, for field programmable gate array to implement one or more instructions as described herein. The instructions of the tangible medium can be implemented by the processor of the control electronics.

The generated UF light beam 6 proceeds towards the patient eye 68 passing through a half-wave plate 8 and a linear polarizer, 10. The polarization state of the beam can be adjusted so that the desired amount of light passes through the half-wave plate 8 and the linear polarizer 10, which together act as a variable attenuator for the UF beam 6. Additionally, the orientation of the linear polarizer 10 determines the incident polarization state incident upon a beam combiner 34, thereby optimizing the beam combiner 34 throughput.

The UF light beam 6 proceeds through a system-controlled shutter 12, an aperture 14, and a pickoff device 16. The system-controlled shutter 12 ensures on/off control of the laser for procedural and safety reasons. The aperture 14 sets an outer useful diameter for the UF light beam 6 and the pickoff device 16 monitors the resulting beam. The pickoff device 16 includes a partially reflecting mirror 20 and a detector 18. Pulse energy, average power, or a combination can be measured using the detector 18. Output from the detector 18 can be used for feedback to the half-wave plate 8 for attenuation and to verify whether the system-controlled shutter 12 is open or closed. In addition, the system-controlled shutter 12 can have position sensors to provide a redundant state detection.

The beam passes through a beam conditioning stage 22, in which beam parameters such as beam diameter, divergence, circularity, and astigmatism can be modified. In this illustrative example, the beam conditioning stage 22 includes a two-element beam expanding telescope comprised of spherical optics 24, 26 in order to achieve the intended beam size and collimation. Although not illustrated here, an anamorphic or other optical system can be used to achieve the desired beam parameters. The factors used to determine these beam parameters include the output beam parameters of the laser, the overall magnification of the system, and the desired numerical aperture (NA) at the treatment location. In addition, the beam conditioning stage 22 can be used to image aperture 14 to a desired location (e.g., the center location between a 2-axis scanning device 50 described below). In this way, the amount of light that makes it through the aperture 14 is assured to make it through the scanning system. The pickoff device 16 is then a reliable measure of the usable light.

After exiting the beam conditioning stage 22, the beam 6 reflects off of fold mirrors 28, 30, 32. These mirrors can be adjustable for alignment purposes. The beam 6 is then incident upon the beam combiner 34. The beam combiner 34 reflects the UF beam 6 (and transmits both the imaging, in this exemplary case, an optical coherence tomography (OCT) beam 114, and an aim 202 beam described below). For efficient beam combiner operation, the angle of incidence is preferably kept below 45 degrees and the polarization of the beams is fixed where possible. For the UF beam 6, the orientation of the linear polarizer 10 provides fixed polarization. Although OCT is used as the imaging modality in this non-limiting example, other approaches, such as Purkinje imaging, Scheimpflug imaging, confocal or non-linear optical microscopy, fluorescence imaging, ultrasound, structured light, stereo imaging, or other known ophthalmic or medical imaging modalities and/or combinations thereof may be employed.

Following the beam combiner 34, the beam 6 continues onto a z-adjust or Z scan device 40. In this illustrative example the z-adjust 40 includes a Galilean telescope with two lens groups 42, 44 (each lens group includes one or more lenses). The lens group 42 moves along the z-axis about the collimation position of the telescope. In this way, the focus position of the spot in the patient's eye 68 moves along the z-axis as indicated. In general, there is a fixed linear relationship between the motion of lens 42 and the motion of the focus. In this case, the z-adjust telescope has an approximate 2× beam expansion ratio and a 1:1 relationship of the movement of lens 42 to the movement of the focus. Alternatively, the lens group 44 could be moved along the z-axis to actuate the z-adjust, and scan. The z-adjust 40 is the z-scan device for treatment in the eye 68. It can be controlled automatically and dynamically by the system and selected to be independent or to interplay with the X-Y scan device described next. The mirrors 36, 38 can be used for aligning the optical axis with the axis of the z-adjust device 40.

After passing through the z-adjust device 40, the beam 6 is directed to the x-y scan device 50 by mirrors 46, 48. The mirrors 46, 48 can be adjustable for alignment purposes. X-Y scanning is achieved by the scanning device 50 preferably using two mirrors 52, 54 under the control of the control electronics 300, which rotate in orthogonal directions using motors, galvanometers, or any other well known optic moving device. The mirrors 52, 54 are located near the telecentric position of an objective lens 58 and a contact lens 66 combination described below. Tilting the mirrors 52, 54 changes the resulting direction of the beam 6, causing lateral displacements in the plane of UF focus located in the patient's eye 68. The objective lens 58 may be a complex multi-element lens element, as shown, and represented by lenses 60, 62, and 64. The complexity of the objective lens 58 will be dictated by the scan field size, the focused spot size, the available working distance on both the proximal and distal sides of objective lens 58, as well as the amount of aberration control. An f-theta objective lens 58 of focal length 60 mm generating a spot size of 10 μm, over a field of 10 mm, with an input beam size of 15 mm diameter is an example. Alternatively, X-Y scanning by the scanning device 50 may be achieved by using one or more moveable optical elements (e.g., lenses, gratings), which also may be controlled by the control electronics 300, via the input and output device 302.

The scanning device 50 under the control of the control electronics 300 can automatically generate the aiming and treatment scan patterns. Such patterns may be comprised of a single spot of light, multiple spots of light, a continuous pattern of light, multiple continuous patterns of light, and/or any combination of these. In addition, the aiming pattern (using the aim beam 202 described below) need not be identical to the treatment pattern (using the light beam 6), but preferably at least defines its boundaries in order to assure that the treatment light is delivered only within the desired target area for patient safety. This may be done, for example, by having the aiming pattern provide an outline of the intended treatment pattern. This way the spatial extent of the treatment pattern may be made known to the user, if not the exact locations of the individual spots themselves, and the scanning thus optimized for speed, efficiency and accuracy. The aiming pattern may also be made to be perceived as blinking in order to further enhance its visibility to the user.

An optional contact lens 66, which can be any suitable ophthalmic lens, can be used to help further focus the light beam 6 into the patient's eye 68 while helping to stabilize eye position. The positioning and character of the light beam 6 and/or the scan pattern the light beam 6 forms on the eye 68 may be further controlled by use of an input device such as a joystick, or any other appropriate user input device (e.g., GUI 304) to position the patient and/or the optical system.

The UF laser 4 and the control electronics 300 can be set to target the targeted structures in the eye 68 and ensure that the light beam 6 will be focused where appropriate and not unintentionally damage non-targeted tissue. Imaging modalities and techniques described herein, such as those mentioned above, or ultrasound may be used to determine the location and measure the thickness of the lens and lens capsule to provide greater precision to the laser focusing methods, including 2D and 3D patterning. Laser focusing may also be accomplished using one or more methods including direct observation of an aiming beam, or other known ophthalmic or medical imaging modalities, such as those mentioned above, and/or combinations thereof. In the embodiment of FIG. 1, an OCT device 100 is described, although other modalities are within the scope of the present invention. An OCT scan of the eye will provide information about the axial location of the anterior and posterior lens capsule, the boundaries of the cataract nucleus, as well as the depth of the anterior chamber. This information is then loaded into the control electronics 300, and used to program and control the subsequent laser-assisted surgical procedure. The information may also be used to determine a wide variety of parameters related to the procedure such as, for example, the upper and lower axial limits of the focal planes used for cutting the lens capsule and segmentation of the lens cortex and nucleus, and the thickness of the lens capsule among others.

The OCT device 100 in FIG. 1 includes a broadband or a swept light source 102 that is split by a fiber coupler 104 into a reference arm 106 and a sample arm 110. The reference arm 106 includes a module 108 containing a reference reflection along with suitable dispersion and path length compensation. The sample arm 110 of the OCT device 100 has an output connector 112 that serves as an interface to the rest of the UF laser system. The return signals from both the reference and sample arms 106, 110 are then directed by coupler 104 to a detection device 128, which employs a time domain detection technique, a frequency detection technique, or a single point detection technique. In FIG. 1, a frequency domain technique is used with an OCT wavelength of 830 nm and bandwidth of 100 nm.

After exiting the connector 112, the OCT beam 114 is collimated using a lens 116. The size of the collimated OCT beam 114 is determined by the focal length of the lens 116. The size of the beam 114 is dictated by the desired NA at the focus in the eye and the magnification of the beam train leading to the eye 68. Generally, the OCT beam 114 does not require as high an NA as the UF light beam 6 in the focal plane and therefore the OCT beam 114 is smaller in diameter than the UF light beam 6 at the beam combiner 34 location. Following the collimating lens 116 is an aperture 118, which further modifies the resultant NA of the OCT beam 114 at the eye. The diameter of the aperture 118 is chosen to optimize OCT light incident on the target tissue and the strength of the return signal. A polarization control element 120, which may be active or dynamic, is used to compensate for polarization state changes. The polarization state changes may be induced, for example, by individual differences in corneal birefringence. Mirrors 122, 124 are then used to direct the OCT beam 114 towards beam combiners 126, 34. Mirrors 122, 124 can be adjustable for alignment purposes and in particular for overlaying of the OCT beam 114 to the UF light beam 6 subsequent to the beam combiner 34. Similarly, the beam combiner 126 is used to combine the OCT beam 114 with the aim beam 202 as described below.

Once combined with the UF light beam 6 subsequent to beam combiner 34, the OCT beam 114 follows the same path as the UF light beam 6 through the rest of the system. In this way, the OCT beam 114 is indicative of the location of the UF light beam 6. The OCT beam 114 passes through the z-scan 40 and x-y scan 50 devices then the objective lens 58, the contact lens 66, and on into the eye 68. Reflections and scatter off of structures within the eye provide return beams that retrace back through the optical system, into the connector 112, through the coupler 104, and to the OCT detector 128. These return back reflections provide OCT signals that are in turn interpreted by the system as to the location in X, Y, and Z of UF light beam 6 focal location.

The OCT device 100 works on the principle of measuring differences in optical path length between its reference and sample arms. Therefore, passing the OCT beam 114 through the z-adjust device 40 does not extend the z-range of the OCT system 100 because the optical path length does not change as a function of movement of the lens group 42. The OCT system 100 has an inherent z-range that is related to the detection scheme, and in the case of frequency domain detection it is specifically related to the spectrometer and the location of the reference arm 106. In the case of OCT system 100 used in FIG. 1, the z-range is approximately 1-2 mm in an aqueous environment. Extending this range to at least 4 mm involves the adjustment of the path length of the reference arm within OCT system 100. Passing the OCT beam 114 in the sample arm through the z-scan of z-adjust device 40 allows for optimization of the OCT signal strength. This is accomplished by focusing the OCT beam 114 onto the targeted structure while accommodating the extended optical path length by commensurately increasing the path within the reference arm 106 of OCT system 100.

Because of the fundamental differences in the OCT measurement with respect to the UF focus device due to influences such as immersion index, refraction, and aberration, both chromatic and monochromatic, care must be taken in analyzing the OCT signal with respect to the UF beam focal location. A calibration or registration procedure as a function of X, Y, and Z should be conducted in order to match the OCT signal information to the UF focus location and also to the relative to absolute dimensional quantities.

Observation of an aim beam may also be used to assist the user to directing the UF laser focus. Additionally, an aim beam visible to the unaided eye in lieu of the infrared OCT beam and the UF light beam can be helpful with alignment provided the aim beam accurately represents the infrared beam parameters. An aim subsystem 200 is employed in the configuration shown in FIG. 1. The aim beam 202 is generated by an aim beam light source 201, such as a helium-neon laser operating at a wavelength of 633 nm. Alternatively a laser diode in the 630-650 nm range can be used. An advantage of using the helium neon 633 nm beam is its long coherence length, which would enable the use of the aim path as a laser unequal path-length interferometer (LUPI) to measure the optical quality of the beam train, for example.

Once the aim beam light source 201 generates the aim beam 202, the aim beam 202 is collimated using a lens 204. The size of the collimated beam is determined by the focal length of the lens 204. The size of the aim beam 202 is dictated by the desired NA at the focus in the eye and the magnification of the beam train leading to the eye 68. Generally, the aim beam 202 should have close to the same NA as the UF light beam 6 in the focal plane and therefore the aim beam 202 is of similar diameter to the UF light beam 6 at the beam combiner 34. Because the aim beam 202 is meant to stand-in for the UF light beam 6 during system alignment to the target tissue of the eye, much of the aim path mimics the UF path as described previously. The aim beam 202 proceeds through a half-wave plate 206 and a linear polarizer 208. The polarization state of the aim beam 202 can be adjusted so that the desired amount of light passes through the polarizer 208. The half-wave plate 206 and the linear polarizer 208 therefore act as a variable attenuator for the aim beam 202. Additionally, the orientation of polarizer 208 determines the incident polarization state incident upon the beam combiners 126, 34, thereby fixing the polarization state and allowing for optimization of the throughput of the beam combiners 126, 34. Of course, if a semiconductor laser is used as the aim beam light source 200, the drive current can be varied to adjust the optical power.

The aim beam 202 proceeds through a system-controlled shutter 210 and an aperture 212. The system-controlled shutter 210 provides on/off control of the aim beam 202. The aperture 212 sets an outer useful diameter for the aim beam 202 and can be adjusted appropriately. A calibration procedure measuring the output of the aim beam 202 at the eye can be used to set the attenuation of aim beam 202 via control of the polarizer 206.

The aim beam 202 next passes through a beam-conditioning device 214. Beam parameters such as beam diameter, divergence, circularity, and astigmatism can be modified using one or more well known beaming conditioning optical elements. In the case of the aim beam 202 emerging from an optical fiber, the beam-conditioning device 214 can simply include a beam-expanding telescope with two optical elements 216, 218 in order to achieve the intended beam size and collimation. The final factors used to determine the aim beam parameters such as degree of collimation are dictated by what is necessary to match the UF light beam 6 and the aim beam 202 at the location of the eye 68. Chromatic differences can be taken into account by appropriate adjustments of the beam conditioning device 214. In addition, the optical system 214 is used to image aperture 212 to a desired location such as a conjugate location of the aperture 14.

The aim beam 202 next reflects off of fold mirrors 220, 222, which are preferably adjustable for alignment registration to the UF light beam 6 subsequent to the beam combiner 34. The aim beam 202 is then incident upon the beam combiner 126 where the aim beam 202 is combined with the OCT beam 114. The beam combiner 126 reflects the aim beam 202 and transmits the OCT beam 114, which allows for efficient operation of the beam combining functions at both wavelength ranges. Alternatively, the transmit function and the reflect function of the beam combiner 126 can be reversed and the configuration inverted. Subsequent to the beam combiner 126, the aim beam 202 along with the OCT beam 114 is combined with the UF light beam 6 by the beam combiner 34.

A device for imaging the target tissue on or within the eye 68 is shown schematically in FIG. 1 as an imaging system 71. The imaging system 71 includes a camera 74 and an illumination light source 86 for creating an image of the target tissue. The imaging system 71 gathers images that may be used by the control electronics 300 for providing pattern centering about or within a predefined structure. The illumination light source 86 is generally broadband and incoherent. For example, the light source 86 can include multiple LEDs as shown. The wavelength of the illumination light source 86 is preferably in the range of 700 nm to 750 nm, but can be anything that is accommodated by a beam combiner 56, which combines the viewing light with the beam path for the UF light beam 6 and the aim beam 202 (beam combiner 56 reflects the viewing wavelengths while transmitting the OCT and UF wavelengths). The beam combiner 56 may partially transmit the aim wavelength so that the aim beam 202 can be visible to the viewing camera 74. An optional polarization element 84 in front of the light source 86 can be a linear polarizer, a quarter wave plate, a half-wave plate or any combination, and is used to optimize signal. A false color image as generated by the near infrared wavelength is acceptable.

The illumination light from the light source 86 is directed down towards the eye using the same objective lens 58 and the contact lens 66 as the UF light beam 6 and the aim beam 202. The light reflected and scattered off of various structures in the eye 68 are collected by the same lenses 58, 66 and directed back towards the beam combiner 56. At the beam combiner 56, the return light is directed back into the viewing path via beam combiner 56 and a mirror 82, and on to the viewing camera 74. The viewing camera 74 can be, for example but not limited to, any silicon based detector array of the appropriately sized format. A video lens 76 forms an image onto the camera's detector array while optical elements 80, 78 provide polarization control and wavelength filtering respectively. An aperture or iris 81 provides control of imaging NA and therefore depth of focus and depth of field. A small aperture provides the advantage of large depth of field that aids in the patient docking procedure. Alternatively, the illumination and camera paths can be switched. Furthermore, the aim light source 200 can be made to emit infrared light that would not be directly visible, but could be captured and displayed using the imaging system 71.

Coarse adjust registration is usually needed so that when the contact lens 66 comes into contact with the cornea of the eye 68, the targeted structures are in the capture range of the X, Y scan of the system. Therefore a docking procedure is preferred, which preferably takes in account patient motion as the system approaches the contact condition (i.e. contact between the patient's eye 68 and the contact lens 66). The viewing system 71 is configured so that the depth of focus is large enough such that the patient's eye 68 and other salient features may be seen before the contact lens 66 makes contact with the eye 68.

Preferably, a motion control system 70 is integrated into the overall system 2, and may move the patient, the system 2 or elements thereof, or both, to achieve accurate and reliable contact between the contact lens 66 and the eye 68. Furthermore, a vacuum suction subsystem and flange may be incorporated into the system 2, and used to stabilize the eye 68. Alignment of the eye 68 to the system 2 via the contact lens 66 can be accomplished while monitoring the output of the imaging system 71, and performed manually or automatically by analyzing the images produced by the imaging system 71 electronically by means of the control electronics 300 via the IO 302. Force and/or pressure sensor feedback can also be used to discern contact, as well as to initiate the vacuum subsystem. An alternate patient interface can also be used, such as that described in U.S. patent application Ser. No. 13/225,373, which is incorporated herein by reference.

Figure 2:
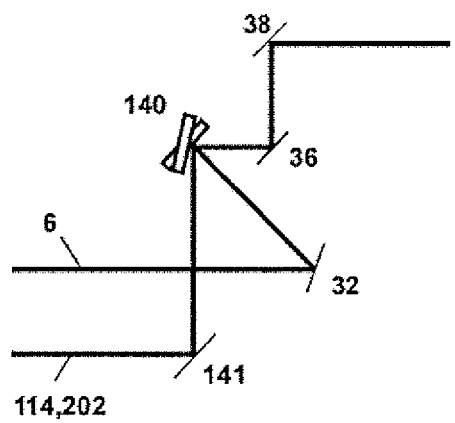
FIG. 2 shows a schematic representation of another embodiment of a system, which utilizes optical multiplexing to deliver treatment and imaging light, capable of creating anchoring capsulotomies, in accordance with many embodiments.

An alternative beam combining configuration is shown in the alternate embodiment of FIG. 2. For example, the passive beam combiner 34 in FIG. 1 can be replaced with an active combiner 140 as shown in FIG. 2. The active beam combiner 140 can be a moving or dynamically controlled element such as a galvanometric scanning mirror, as shown. The active combiner 140 changes its angular orientation in order to direct either the UF light beam 6 or the combined aim and OCT beams 202,114 towards the scanner 50 and eventually towards the eye 68 one at a time. The advantage of the active combining technique is that it avoids the difficulty of combining beams with similar wavelength ranges or polarization states using a passive beam combiner. This ability is traded off against the ability to have simultaneous beams in time and potentially less accuracy and precision due to positional tolerances of active beam combiner 140.

Figure 3:
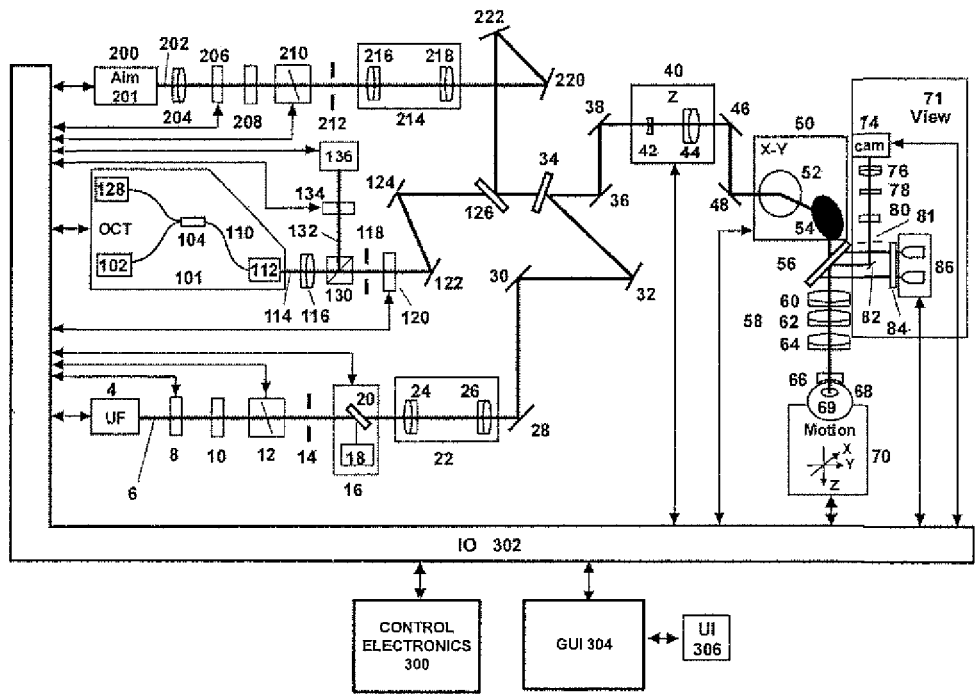
FIG. 3 shows a schematic representation of another embodiment of a system, which utilizes an alternate imaging system, capable of creating anchoring capsulotomies, in accordance with many embodiments.

Another alternate embodiment is shown in FIG. 3 and is similar to that of FIG. 1 but utilizes an alternate approach to the OCT 100. In FIG. 3, an OCT 101 is the same as the OCT 100 in FIG. 1, except that the reference arm 106 has been replaced by a reference arm 132. This free-space OCT reference arm 132 is realized by including a beam splitter 130 after the lens 116. The reference beam 132 then proceeds through a polarization controlling element 134 and then onto a reference return module 136. The reference return module 136 contains the appropriate dispersion and path length adjusting and compensating elements and generates an appropriate reference signal for interference with the sample signal. The sample arm of OCT 101 now originates subsequent to the beam splitter 130. Potential advantages of this free space configuration include separate polarization control and maintenance of the reference and sample arms. The fiber based beam splitter 104 of the OCT 101 can also be replaced by a fiber based circulator. Alternately, both the OCT detector 128 and the beam splitter 130 might be moved together as opposed to the reference return module 136.

Figure 4:
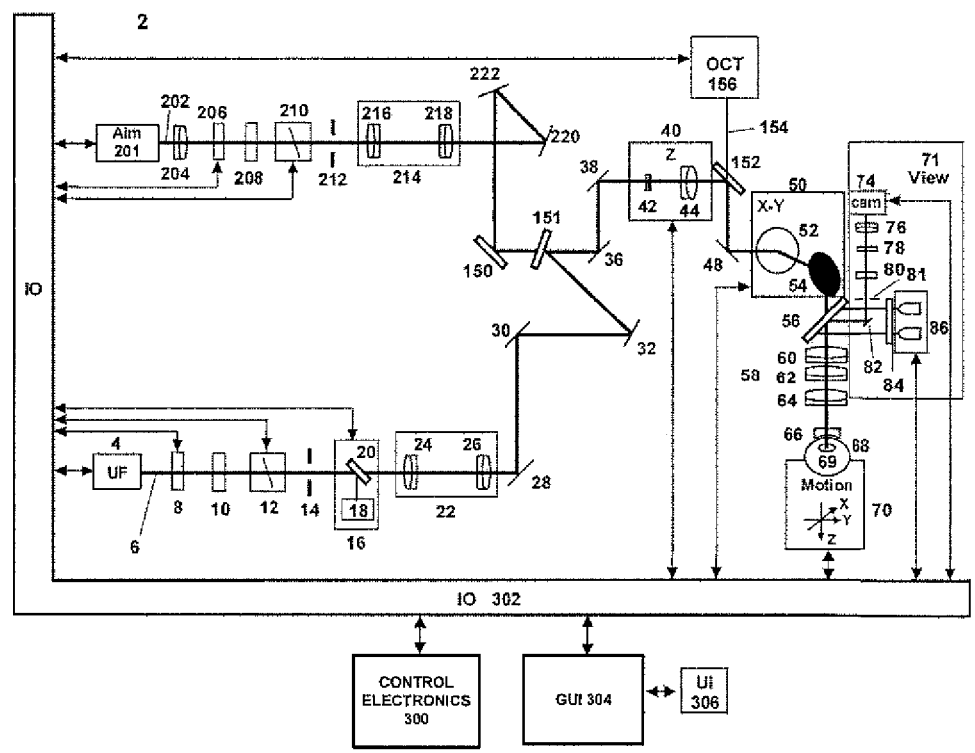
FIG. 4 shows a schematic representation of another embodiment of a system, which utilizes another alternate imaging system configuration, capable of creating anchoring capsultomies, in accordance with many embodiments.

FIG. 4 shows another alternative embodiment for combining the OCT beam 114 and the UF light beam 6. In FIG. 4, an OCT 156 (which can include either of the configurations of OCT 100 or 101) is configured such that an OCT beam 154 output by the OCT 156 is coupled to the UF light beam 6 after the z-scan device 40 using a beam combiner 152. In this way, the OCT beam 154 avoids using the z-scan device 40. This allows the OCT 156 to possibly be folded into the beam more easily and shortening the path length for more stable operation. This OCT configuration is at the expense of an optimized signal return strength as discussed with respect to FIG. 1. There are many possibilities for the configuration of the OCT interferometer, including time and frequency domain approaches, single and dual beam methods, swept source, etc, as described in U.S. Pat. Nos. 5,748,898; 5,748,352; 5,459,570; 6,111,645; and 6,053,613 (which are incorporated herein by reference.)

The system 2 can be set to locate the surface of the capsule and ensure that the light beam 6 will be focused on the lens capsule at all points of the desired opening. Imaging modalities and techniques described herein, such as for example, Optical Coherence Tomography (OCT), such as Purkinje imaging, Scheimpflug imaging, confocal or nonlinear optical microscopy, fluorescence imaging, ultrasound, structured light, stereo imaging, or other known ophthalmic or medical imaging modalities and/or combinations thereof may be used to determine the shape, geometry, perimeter, boundaries, and/or 3-dimensional location of the lens and lens capsule to provide greater precision to the laser focusing methods, including 2D and 3D patterning. Laser focusing may also be accomplished using one or more methods including direct observation of an aiming beam, or other known ophthalmic or medical imaging modalities and combinations thereof, such as but not limited to those defined above.

Optical imaging of the anterior chamber and lens can be performed on the lens using the same laser and/or the same scanner used to produce the patterns for cutting. This scan will provide information about the axial location and shape (and even thickness) of the anterior and posterior lens capsule, the boundaries of the cataract nucleus, as well as the depth of the anterior chamber. This information may then be loaded into the laser 3-D scanning system or used to generate a three dimensional model/representation/image of the anterior chamber and lens of the eye, and used to define the patterns used in the surgical procedure.

Figure 5A:
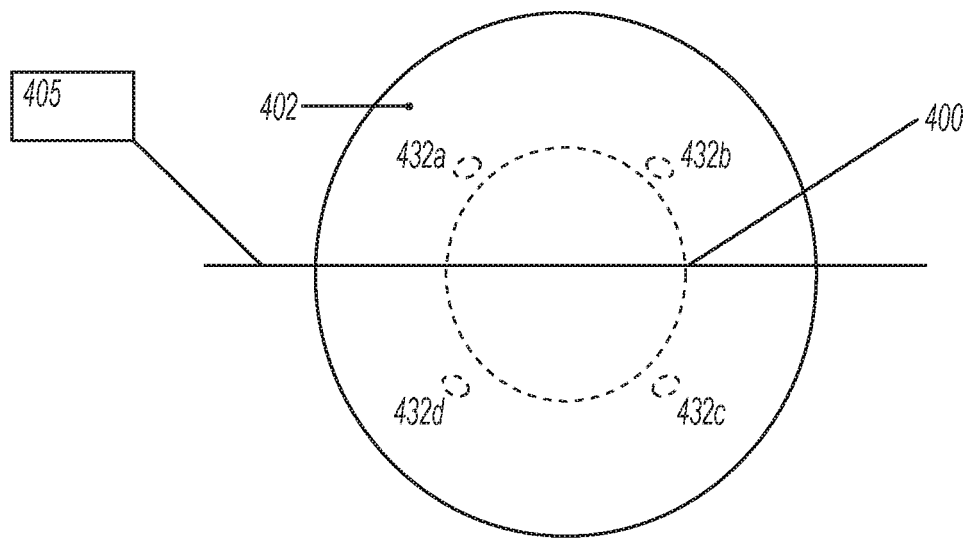
FIGS. 5A and 5B shows example anchoring capsulotomies for constraining an IOL, in accordance with many embodiments.

The above-described systems may be used to incise the capsule of the lens of an eye to produce an anchoring capsulotomy. An example is the array of four anchoring capsulotomies in the lens capsule have been placed at regular spacing circumferentially about a larger capsulotomy that may be used to mate with complementary anchoring features on an IOL that is shown in FIG. 5A. In this example, capsule 402 is incised using the system described above to create anchoring capsulotomies 432A-432D. These microfemtotomies are disposed about the perimeter of a central capsulotomy 400. The central capsulotomy 400 is not required to practice the present invention, but is given as a non-limiting example for the cases where an IOL 440 is to be implanted above an existing IOL (not shown) for which central capsulotomy 400 pre-exists or into the capsule itself where central capsulotomy 400 is used in the traditional manner to provide instrumentation access for removing the crystalline lens during cataract surgery.

In many embodiments the eye comprises aberrations that extend along an aberration axis 405. The aberration axis may comprise one or more of many axes suitable to describe an aberration of the eye such as astigmatism and higher order aberrations, for example. In many embodiments, aberration axis 405 will extend along a horizontal axis of the eye or along a vertical axis of the eye. With astigmatism, a first axis may extend in a first direction and a second axis may extend in a second direction perpendicular to the first direction. In many embodiments, aberration axis 405 will extend away from a horizontal axis of the eye and away from a vertical axis of the eye.

Figure 5B:
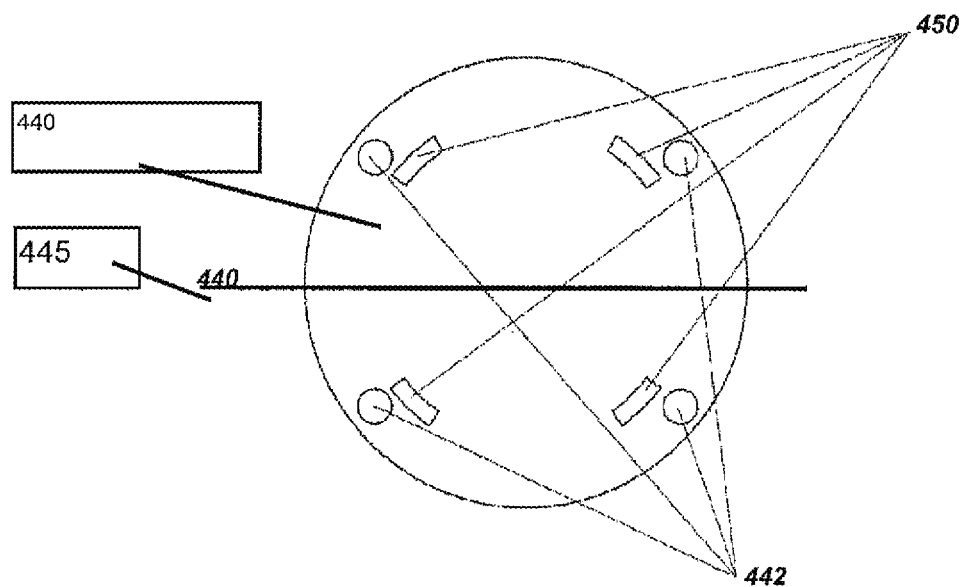

FIG. 5B shows an IOL 440 that is configured to be constrained via the anchoring capsulotomies 432A-432D. In this non-limiting example, the IOL 440 is configured with anchors 442 that are configured to engage the anchoring capsulotomies 432A-432D, as well as struts 450. The struts 450 are intended to maintain a prescribed distance between the IOL 440 and the capsule 402. This is discussed in more detail in the following section on posterior capsule opacification, also known as "secondary cataract." The anchoring capsulotomy incisions may be too small to be created reliably by hand. Likewise, the required placement of the anchoring capsulotomy incisions can be very precise. There is a myriad of possibilities for employing such mating anchoring capsulotomies and IOL anchoring features that provide for the improved placement of an IOL relative to the lens capsule of the eye of a patient. European Pat. Appl. No. EPP16613A-100927 discloses similar IOLs, which are included herein by reference.

In many embodiments, IOL 440 comprises a shape to correct aberrations of the eye and an aberration correcting axis 445. The aberration correcting axis 445 can be aligned in relation to anchors 442, for example with a pre-determined alignment with respect to anchors 442. The anchors 442 can be located so as to align the aberration correcting axis 445 with the aberration axis 405 in order to treat an aberration of the eye such as one or more of astigmatism or higher order aberrations of the eye.

Figure 6A:
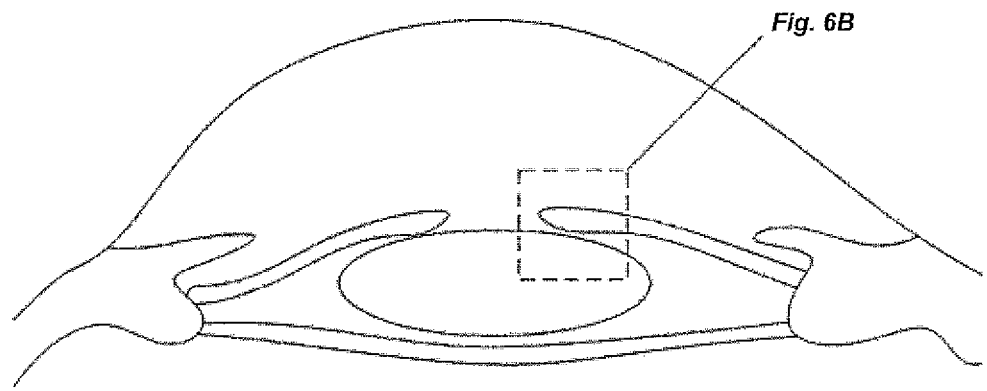
FIGS. 6A and 6B show an IOL being constrained within the lens capsule using anchoring capsulotomies, in accordance with an embodiment, in accordance with many embodiments.
Figure 6B:
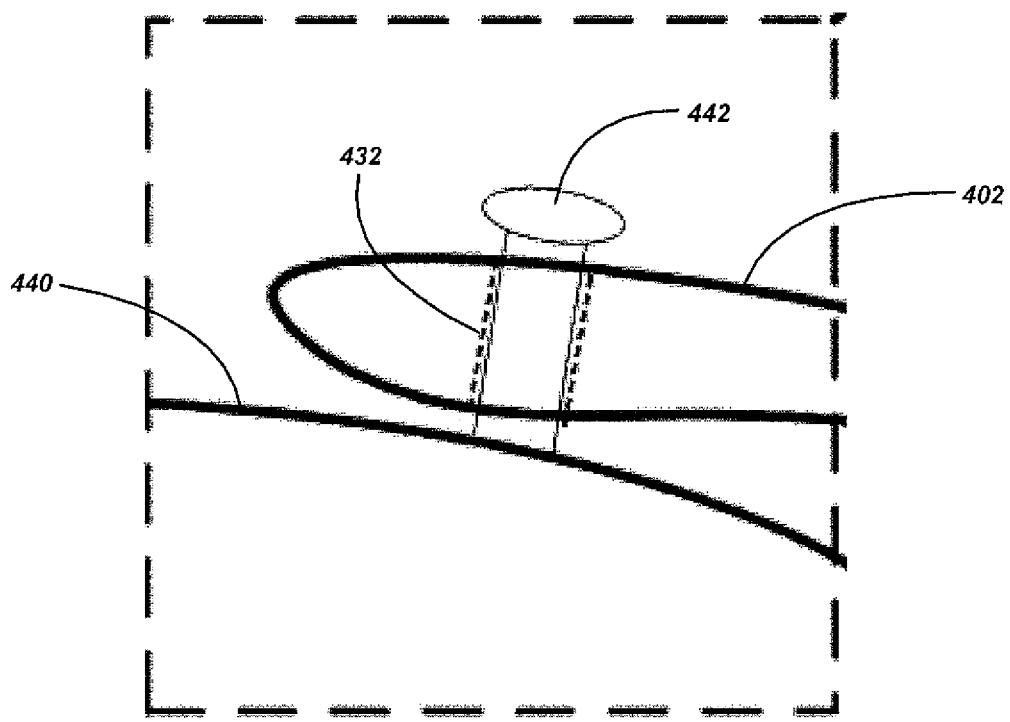

FIGS. 6A and 6B show more anatomical details of the above-mentioned embodiment in which a microfemtotomy 432 is used to secure the IOL 440 of FIG. 5B within the lens capsule 402 by means of the anchors 442.

The anchoring capsulotomy need not be round, as shown in the previous examples, and again in FIG. 7A. As non-limiting examples, FIGS. 7A through 7C show a few useful anchoring capsulotomy shapes that can be used. In general, any suitably shaped anchoring capsulotomy can be used. FIGS. 7B and 7C show two exemplary alternate configurations of elliptical and rectangular anchoring capsulotomy shape perimeters. An elliptical and/or a rectangular anchoring capsulotomy shaped perimeter can be used in the buttonhole concept mentioned above. The perimeters shown in FIGS. 7B and 7C contain both long and short margins.

The tip of each anchor may be inserted into a corresponding capsulotomy and pushed through to capture the anchor and hold the anchor in place once engaged. As such, the tip of the anchor should be overall larger than the buttonhole incision of the anchoring capsulotomy. This can be thought of as analogous to a buttonhole holding a button. Alternately, a buttonhole capsulotomy can be constructed using a single linear incision. Such a linear incision can be made such that is tangential, or close to tangential, to a circle describing the matching posts of the IOL to be implanted. Thus, the IOL can be implanted buy inserting each post individually, as opposed to requiring the posts to all be in more or less in place as would be the case when the incisions are more or less perpendicular to a circle describing the location of the posts of the IOL to be implanted.

The incisions can also be made such that they are nominally linear and include rounded edges, forming a "bone-shaped" incision. Similarly, a teardrop-shaped or rounded-point-teardrop-shaped incision can also be formed.

In a further alternate embodiment, a small capsulotomy can be made such that it is substantially square, as opposed to rectangular. Although not shown in the accompanying figures, the corners of small capsulotomies containing substantially linear edges can be made rounded to minimize the risk of capsular incision extension due to strain concentration at sharp corners. The creation of such small capsulotomies, especially with smoothly rounded edges, is practically impossible to perform manually.

FIGS. 8A and 8B show an alternate embodiment wherein the IOL 440 to be implanted is placed above an existing ocular lens 444. This is alternatively referred to herein as "piggybacking" and is particularly useful in cases where the removal of the existing ocular lens 444 (either the natural crystalline lens or an artificial implant) is not accomplished. The implantation of such an additional lens 440 may be desirable in certain cases such as in cases of juvenile cataracts or other situations where the patient's refraction changes appreciably over time. In such cases, even though the eye must be invaded, the risks associated with removing an existing implant 444 are avoided by implanting the IOL 440 over the existing lens 444 in the anterior chamber. Such an IOL can be configured to improve the balance of the patient's optical system. This can be achieved in cases of hyperopia and myopia by the introduction of optical elements such as positive and negative spherical lenses, respectively. Tonic elements such as cylindrical lenses, optical wedges and gradient index materials may also be used to correct astigmatism and even to address higher order aberrations such as coma.

Figure 9A:
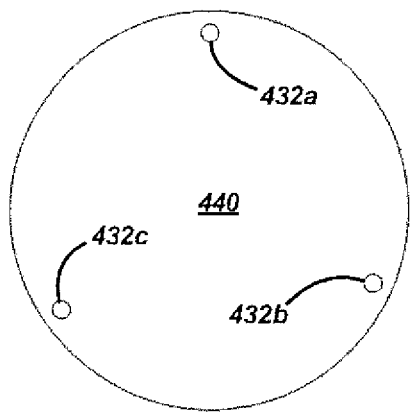
FIGS. 9A through 9D show examples of different IOL anchoring capsulotomy configurations, in accordance with many embodiments.
Figure 9C:
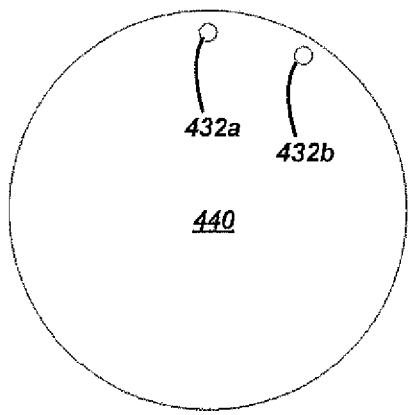
Figure 9B:
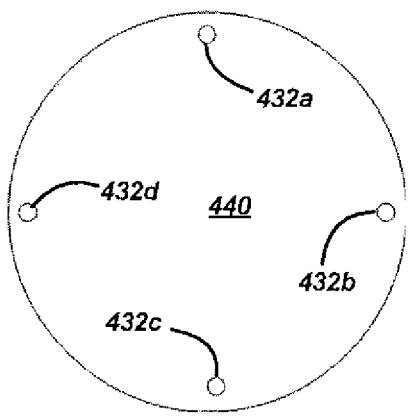
Figure 9D:
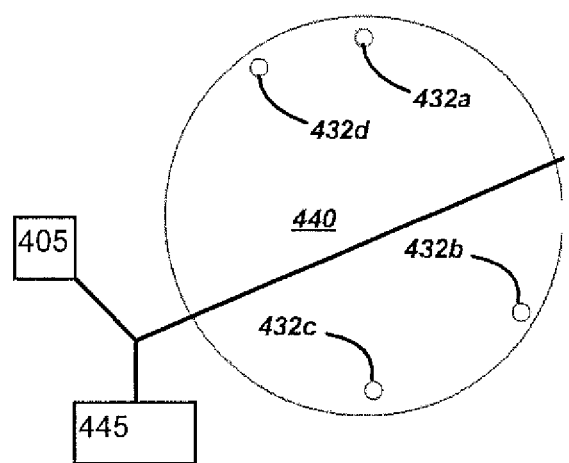

Furthermore, the placement accuracy afforded makes it possible to implant optical elements in the eye of a patient to correct for numerous aberrations. For example, the patient's refraction can be determined by wavefront measurement or other suitable means and the optical correction required to achieve emmetropia determined so that a customized optical implant can be designed. For convenience, we refer to the optical implant as an IOL, though it need not be a conventional lens. This implant (IOL) can then be fabricated such that its implantation orientation is unambiguous. This can be achieved by the use of a rotationally asymmetric configuration of anchors and mating anchoring capsulomotomies such that IOL orientation is "keyed" or "clocked", such as those shown in FIGS. 9A-D. This way an IOL 440 can be placed in the capsule of the eye such that it rotationally locates the IOL with respect to the astigmatic axis of the eye. Such clocking may be accomplished by providing a pattern of microfemtotomies 432A, 432B, 432C, 434D such they form a rotationally asymmetric pattern, such as is shown in FIGS. 9C and 9D. This rotationally asymmetric pattern can be beneficial to ensure that an axis of the IOL is aligned to the correct axis of the eye and not 90 degrees or 120 degrees out of alignment, for example. Alternately, the incision pattern may be made to form a rotationally symmetric pattern, such as is shown in FIGS. 9A and 9B. Similar schemes can be employed, such as bilaterally symmetric and bilaterally asymmetric patterns. The patterns can be centered on the eye.

In many embodiments, the aberration axis 405 of the eye is aligned with the aberration correcting axis 445 of the IOL. The pattern of microfemtotomies 432A, 432B, 432C, 434D can be located on the capsule so as to align the aberration correcting axis 445 of the lens with the aberration axis 405 of the eye.

Rotational orientation of the IOL, or providing for rotational indexing about the geometric or optical axes of the eye, can also be provided by making one of a plurality of the microfemtotomies different than the other microfemtotomies in the pattern. This affords the ability to distinguish the asymmetric axis of the eye and/or the IOL to be implanted. With this distinction, a surgeon can locate matching features to assure the correct alignment of the IOL in the patient's eye. The IOL used to mate with these incisions can be made with posts that are not identical to improve its clinical utility.

Similarly, the transverse location (i.e. the lateral location of the microfemtotomies on the capsule can be used to improve the visual outcome of the procedure. The presence of an asymmetric pupil or a pseudo fovea may indicate a lateral alignment that is not as would be expected otherwise. That is, such ophthalmic asymmetries would lead to IOL positions that would not be predicted by simply looking at the anatomy. The present system and method are particularly suited to address these anomalies because of the accuracy and flexibility afforded by the integration of anatomical imaging and laser capsulotomy creation, especially when the integrated imaging systems are used to provide for incision placement relative to anatomical landmarks or other such fiducials.

This concept may be extended to accommodate the natural asymmetry of capsular contraction by orienting an asymmetric pattern of incisions intended to engage with the posts of an IOL by locating the majority of the posts towards the direction of the lowest radial force.

Lens epithelial cells (LECs) that remain in the capsule after lens removal can be problematic. The differentiation of LECs into fibroblast-like cells can cause wrinkles, folds, and opacities ("secondary cataract") of the capsule and can result in posterior capsule opacification (PCO) and TOL decentralization. It has been reported that Posterior capsule opacification causes a decrease in visual acuity in the first 5 years after cataract surgery in more than 25% of patients. Over 2-4 weeks after surgery, the formation of fibrous tissue in the capsule often occurs, pushing the lens back onto the posterior capsule. With conventional square-edged IOLs, a mechanical barrier to migrating LECs on the posterior edge of the lens is created where the square edge barrier is located, such that the central visual field is kept free of PCO. PCO may be avoided in two distinctly different ways using the IOL devices described herein, and in a third way using an implanted drug-eluting device (such as a plug or pellet) to combat PCO via the release of therapeutic agents such as the non-limiting examples of diclofenac sodium, ketorolac tromethamine, and cytotoxic LEC-specific genes.

Tightly sealing the capsule to prevent the proliferation of lens epithelial cells that cause both opacification and mechanical nonconformities in the capsule that serve to dislocate the IOL over time and alter the patient's refractive correction may be accomplished by fabricating the mating IOL such that the lens forms a seal on the capsule about each anchoring capsulotomy and also about the larger central capsulotomy. A second approach is to maintain an open capsule that is in fluid communication with the anterior chamber to minimize the risks instigating epithelial cell proliferation and/or differentiation by diluting the offending cytokines and other agents.

Most traditional IOLs do not consistently provide a complete circumferential seal due to the mechanical discontinuity of the lens-haptic junction. This fundamental limitation provides a pathway for LEC migration and subsequent PCO. Providing a sealed system using the anchoring capsulotomy mating IOL is more readily achieved in the absence of these traditional haptics. Furthermore, a set of matching anchoring capsulotomies can be made in the posterior capsule, as well. These will serve to collapse the capsule and improve the seal. It also has the advantage of enabling the eye's accommodative processes to impart more force on the IOL to move it for improved focus.

Alternately, the present inventive IOL design can provide gaps between the lens and the capsule, at least in places in order to maintain fluid communication between the capsule and the anterior chamber. This will allow for fluid to flow through the anterior chamber and the capsule interior. The non-limiting example IOL shown in FIG. 5B contains stand-off features 450 for this purpose. Other configurations are also possible, such as providing hollow channels within the anchoring features 442, for example.

Alternately, the lens can be implanted within the anterior capsule, the posterior capsule, or both the anterior and posterior capsules. The latter is an alternative to what is known in the art as a "Bag-in-Lens" configuration that may better provide for the eye's accommodative processes. Lenses implanted by the methods described herein may be made intracapsularly on the anterior and/or posterior capsules, or on the anterior and/or posterior extremes of the capsule itself.

IOLs can be made to have axially symmetric posts for engaging with the anterior and posterior capsules. IOLs can also be made such that the posts are not axially symmetric. That is, the posts need not be laterally collocated, even as mirror-images. As such, one can see the bases of all the posts when looking at an IOL from one face.

As mentioned above, alternate embodiments include the use of a microfemtotomy to support a drug-eluting device instead of, or in addition to, an IOL. There are many ongoing ophthalmic needs that are not properly addressed by the present methods of time-release drug placement. Non-limiting examples of this are glaucoma medications; anti-VEGF treatments; and the release of therapeutic agents such as diclofenac sodium, ketorolac tromethamine, and cytotoxic LEC-specific genes to combat PCO; as well as other compounds to improve the chemical diffusion or pumping of the cornea.

Figure 10:
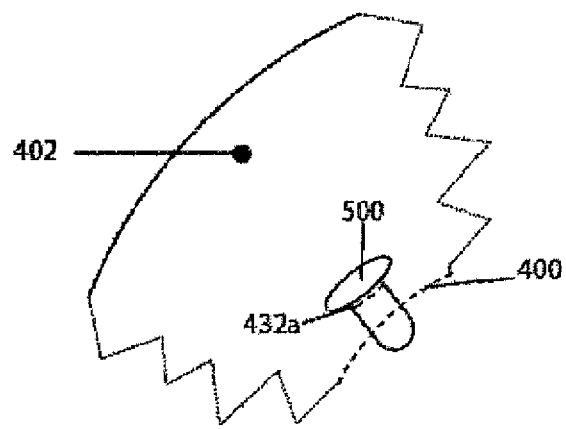
FIG. 10 shows using an anchoring capsulotomy to accommodate an implanted drug-eluting device, in accordance with an embodiment, in accordance with many embodiments.

FIG. 10 shows an embodiment of a drug-eluting device implanted in an anchoring capsulotomy 432a. In this example, drug-eluting device is a plug 500, which is implanted in the anchoring capsulotomy 432a adjacent to a central capsulotomy 400 on the capsule 402. In this example, the plug 500 contains mechanical features designed to retain it in the anchoring capsulotomy 432a.

Figure 11:
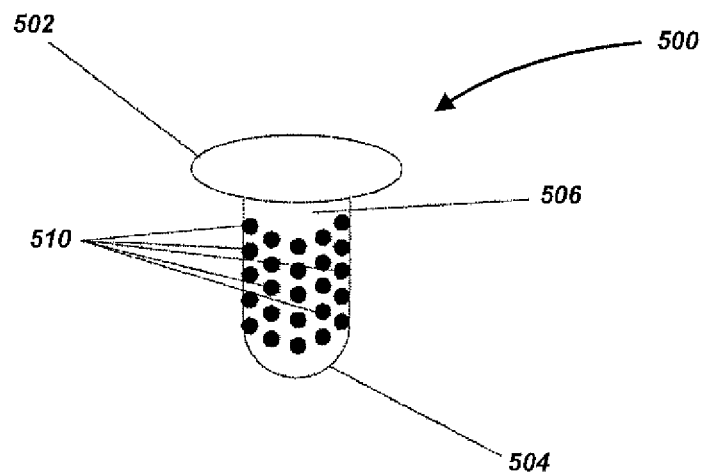
FIG. 11 shows an alternate configuration of an implantable drug-eluting device that is accommodated by an anchoring capsulotomy, in accordance with many embodiments.

The drug-eluting plug 500 shown in FIG. 11 has a cap 502 on a body 506, which ends at an end 504. Pores 510 are included on the body 506 to allow for dispersion of the drug that is otherwise contained within drug-eluting plug 500. Example dimensions of the mechanical features of device 500 are as follows:

| Feature | Nominal Dimension | Range of Dimensions | Units |
| --- | --- | --- | --- |
| Cap 502, outer diameter | 2 | 0.5-4.0 | mm |
| Cap 502, thickness | 0.5 | 0.1-1.0 | mm |
| Body 506, outer diameter | 1 | 1.0-3.0 | mm |
| Body 506, length | 2 | 1.0-3.0 | mm |
| End 504, radius of curvature | 0.5 | 0.125-4.0 | mm |

Figure 12:
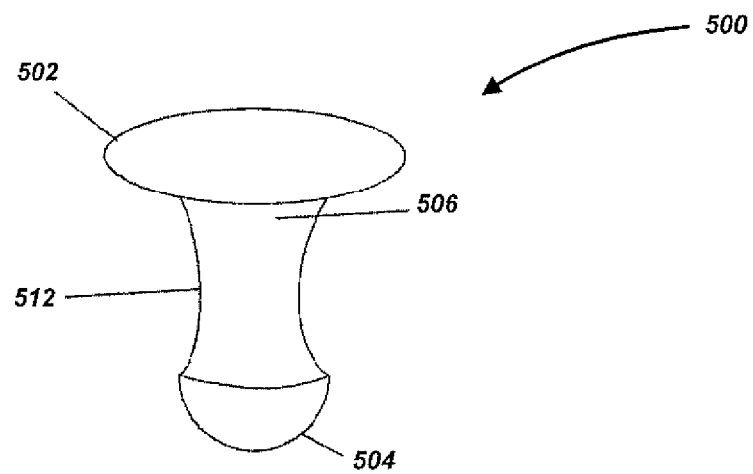
FIG. 12 shows another alternate configuration of an implantable drug-eluting device that is accommodated by an anchoring capsulotomy, in accordance with many embodiments.

FIG. 12 shows a further alternate embodiment of a drug-eluting device for use with an anchoring capsulotomy. Although otherwise similar to the embodiment of FIG. 11, the embodiment shown in FIG. 12 includes the addition of a waist 512 along the body 506 to provide for improved retention of the device 500 within the anchoring capsulotomy 432. Alternately, a buttonhole capsulotomy can be used to provide enhanced retention and support of the device 500.

Figure 13A:
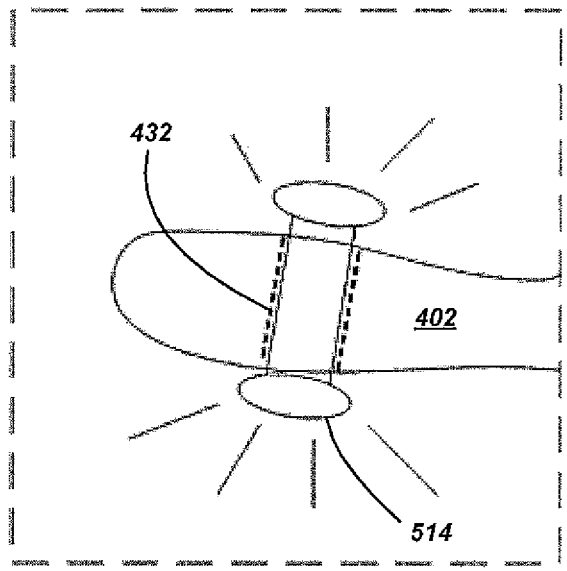
FIGS. 13A and 13B show an alternate configuration of an implanted drug-eluting device that is accommodated in different locations by anchoring capsulotomies, in accordance with many embodiments.
Figure 13B:
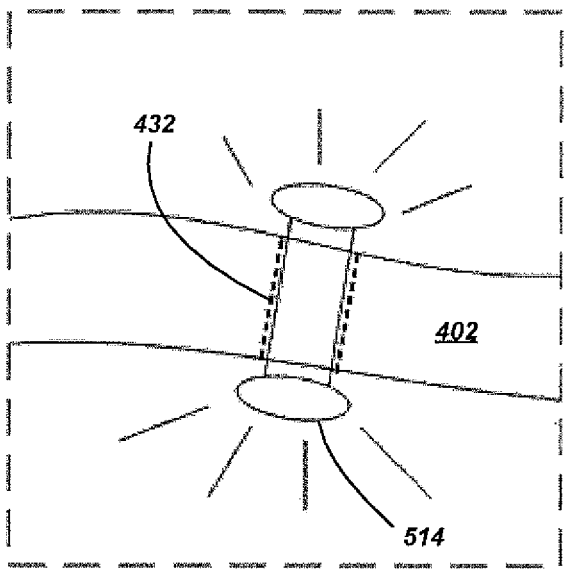

Similar to the device shown in FIGS. 5A through 6B, the alternate embodiment shown in FIG. 13A includes the addition of an end cap 514 to provide improved retention within the anchoring capsulotomy 432. FIG. 13B shows the same device deployed in an area of capsule that is not adjacent to the central capsulotomy.

Figure 14:
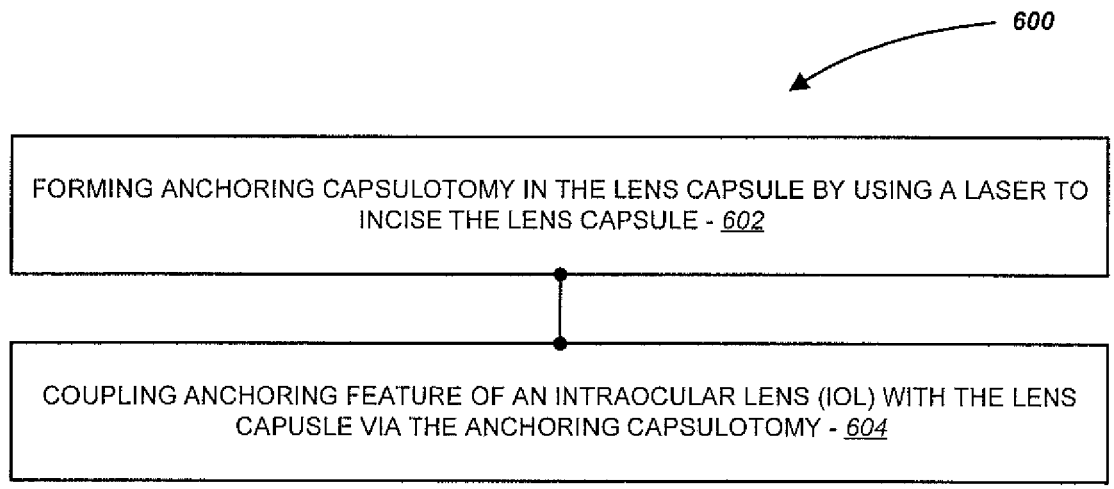
FIG. 14 illustrates a method for creating an anchoring capsulotomy and coupling an anchoring feature of an intraocular lens with the anchoring capsulotomy, in accordance with many embodiments, in accordance with many embodiments.

FIG. 14 illustrates a method 600 for performing laser-assisted surgery on an eye, in accordance with many embodiments. Any suitable system can be used to practice the method 600, including any suitable system disclosed herein.

In step 602, an anchoring capsulotomy is formed in the lens capsule of the eye by using a laser to incise the lens capsule. The anchoring capsulotomy is configured to accommodate an anchoring feature of an intraocular lens (IOL) using any suitable approach, for example, as disclosed herein. In many embodiments, the anchoring feature protrudes transverse to a surface of the IOL that interfaces with the lens capsule adjacent to the lens capsulotomy, such as illustrated in FIG. 6B. The anchoring capsulotomy can have any suitable shape including, for example, button hole, linear, bone-shaped, teardrop-shaped, round, rectangular with round corners, rectangular with sharp corners, and elliptical. Any suitable number of anchoring capsulotomies can be formed in the lens capsule. The one or more anchoring capsulotomies can be placed in any suitable location such as, for example, in the anterior capsule, in the posterior capsule, and in both the anterior and the posterior capsules. Each of a plurality of anchoring capsulotomies can be configured to accommodate a corresponding anchoring feature of an IOL. When multiple anchoring capsulotomies are used, the same or different shapes can be used. In many embodiments, the anchoring capsulotomies and the IOL are configured to orient the IOL relative to the eye to provide correction of astigmatism of the eye. The anchoring capsulotomies can be arranged such that the form a suitable pattern including, for example, a rotationally symmetric pattern, a rotationally asymmetric pattern, a bilaterally symmetric pattern, and a bilaterally asymmetric pattern. The asymmetry of the pattern can be oriented such that it corresponds to a direction of natural asymmetry of capsular contraction. In many embodiments, at least one of the anchoring capsulotomies is elongated tangential to a circle passing through the anchoring features of the IOL when the IOL is implanted. And at least one of the anchoring features can protrude transverse to a surface of the IOL that interfaces with the lens capsule adjacent to the corresponding anchoring capsulotomy.

In step 604, an anchoring feature of the IOL is coupled with the anchoring capsulotomy. The IOL can be placed in any suitable location. For example, the IOL can be placed within the anterior chamber, on or within the lens capsule, on the anterior side of the posterior capsule, and on the posterior side of the anterior capsule. The IOL can be a "piggyback" IOL. A second IOL can be coupled to the lens capsule so that both the IOL and the second IOL are coupled to the lens capsule. The second IOL can be positioned anteriorly relative to the IOL. The orientation of the second IOL relative to the lens capsule can be restrained using two or more anchoring capsulotomies created through the lens capsule with the laser.

Although the above steps show method 600 of treating an eye in accordance with embodiments, a person of ordinary skill in the art will recognize many variations based on the teaching described herein. The steps may be completed in a different order. Steps may be added or deleted. Some of the steps may comprise sub-steps. Many of the steps may be repeated as often as if beneficial to the treatment.

One or more of the steps of the method 600 may be performed with the circuitry as described herein, for example one or more of the processor or logic circuitry such as the programmable array logic for field programmable gate array. The circuitry may be programmed to provide one or more of the steps of method 600, and the program may comprise program instructions stored on a computer readable memory or programmed steps of the logic circuitry such as the programmable array logic or the field programmable gate array, for example.

Figure 15:
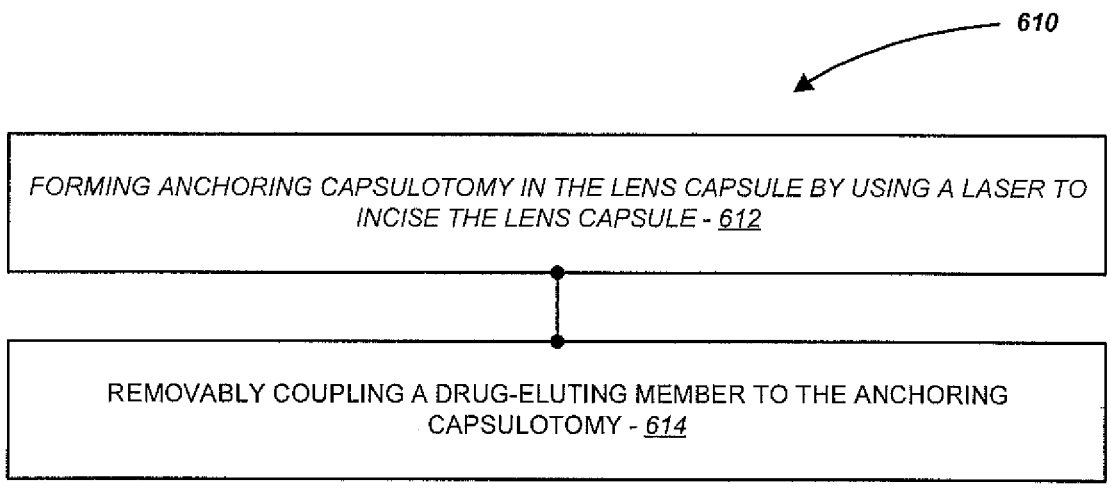
FIG. 15 illustrates a method for creating an anchoring capsulotomy and removably coupling a drug-eluting member to the anchoring capsulotomy, in accordance with many embodiments.

FIG. 15 illustrates a method 610 for performing laser-assisted surgery on an eye, in accordance with many embodiments. Any suitable system can be used to practice the method 610, including any suitable system disclosed herein.

In step 612, an anchoring capsulotomy is formed in the lens capsule of the eye by using a laser to incise the lens capsule. The anchoring capsulotomy is configured to accommodate a drug-eluting member using any suitable approach, for example, as disclosed herein. And more than one anchoring capsulotomy configured to accommodate a drug-eluting member can be formed and/or located in any suitable location including, for example, in the anterior capsule, in the posterior capsule, or in both the anterior and posterior capsules.

In step 614, the drug-eluting member is removably coupled to the anchoring capsulotomy. A mechanical feature of the drug-eluting member can be removably fitted through the anchoring capsulotomy to retain the drug-eluting member's position relative to the lens capsule. One or more additional drug-eluting members can be removably coupled with corresponding additional anchoring capsulotomies.

Although the above steps show method 610 in accordance with embodiments, a person of ordinary skill in the art will recognize many variations based on the teaching described herein. The steps may be completed in a different order. Steps may be added or deleted. Some of the steps may comprise sub-steps. Many of the steps may be repeated as often as if beneficial to the treatment.

One or more of the steps of the method 610 may be performed with the circuitry as described herein, for example one or more of the processor or logic circuitry such as the programmable array logic for field programmable gate array. The circuitry may be programmed to provide one or more of the steps of method 610, and the program may comprise program instructions stored on a computer readable memory or programmed steps of the logic circuitry such as the programmable array logic or the field programmable gate array, for example.

Figure 16:
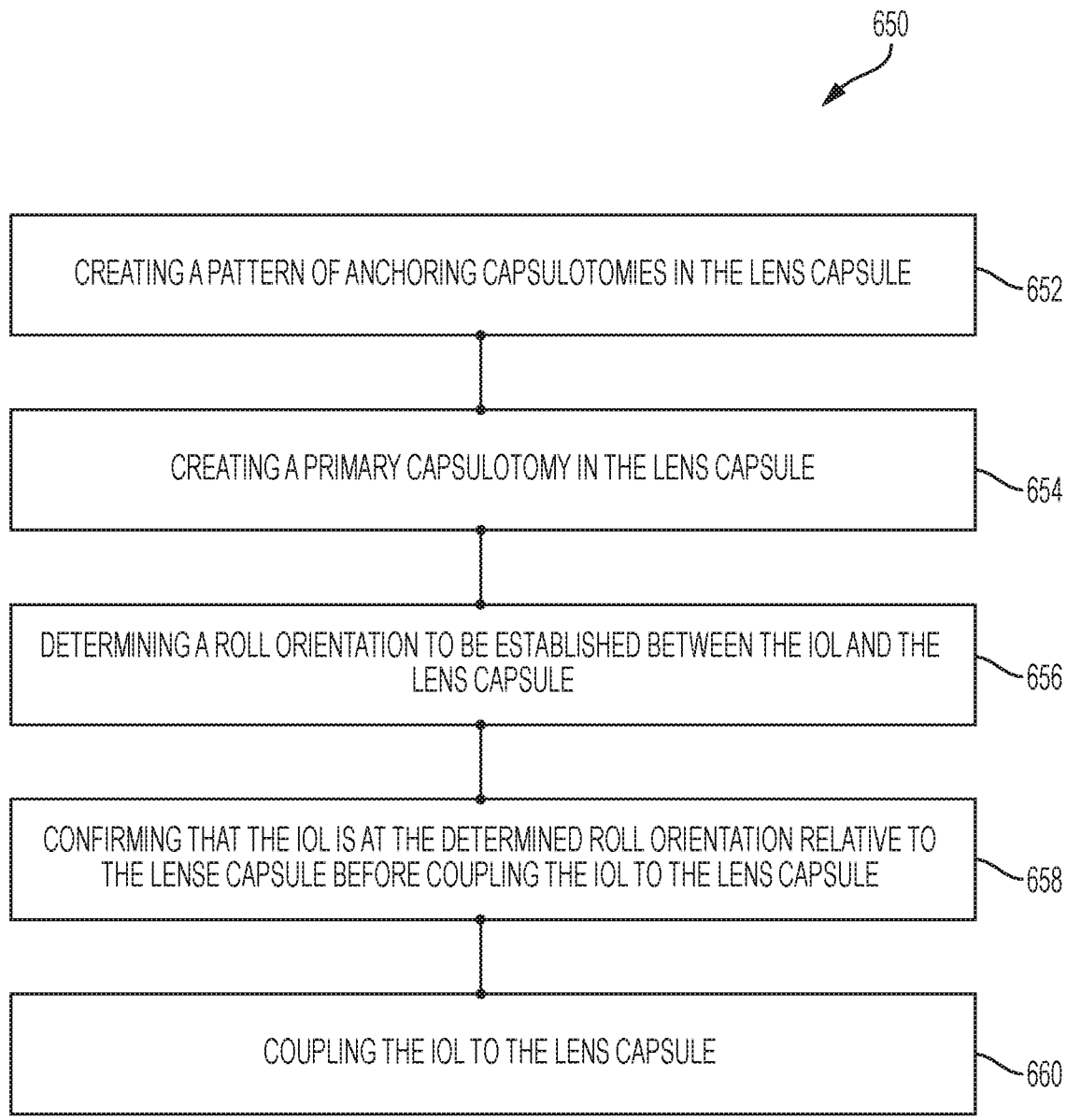
FIG. 16 illustrates a method 650 of ophthalmic intervention, in accordance with many embodiments.

FIG. 16 illustrates a method 650 of ophthalmic intervention, in accordance with many embodiments. Any suitable system can be used to practice the method 650, including any suitable system disclosed herein.

In step 652, a pattern of anchoring capsulotomies is created in a lens capsule of an eye. The pattern of anchoring capsulotomies is configured to be mechanically coupled to anchoring features of an intraocular lens (IOL). Each anchoring capsulotomy of the pattern is configured to accommodate a corresponding anchoring feature of the intraocular lens (IOL) using any suitable approach, for example, as disclosed herein. In many embodiments, at least one of the anchoring features of the pattern protrudes transverse to a surface of the IOL that interfaces with the lens capsule adjacent to the corresponding anchoring capsulotomy, such as illustrated in FIG. 6B. The anchoring capsulotomies of the pattern can have any suitable shape. For example, at least one of the anchoring capsulotomies of the pattern can have a buttonhole shape, a teardrop shape, a round shape, a rectangular shape with sharp corners, a rectangular shape with round corners, a linear shape, a bone shape, and an elliptical shape. In many embodiments, creating the pattern of anchoring capsulotomies includes incising the lens capsule with a laser.

In step 654, a primary capsulotomy is created in the lens capsule. The primary capsulotomy can be an anterior capsulotomy, a posterior capsulotomy, and/or both an anterior capsulotomy and a posterior capsulotomy. The primary capsulotomy can be created to have any suitable boundary shape. For example, the boundary shape of the primary capsulotomy can be circular, elliptical, polygonal, arcuate, and linear. In many embodiments, creating the primary capsulotomy includes incising the lens capsule with a laser.

The anchoring capsulotomies can be placed in any suitable locations around the primary capsulotomy. For example, the creation of the pattern of anchoring capsulotomies can include placing two or more of the anchoring capsulotomies at locations substantially equivalently spaced apart about the boundary of the primary capsulotomy. The creation of the pattern of anchoring capsulotomies can include placing two or more anchoring capsulotomies at locations non-homogeneously spaced apart about the boundary of the primary capsulotomy. The pattern of anchoring capsulotomies can be created to be rotationally symmetric, rotationally asymmetric, bilaterally symmetric, or bilaterally asymmetric.

In step 656, a roll orientation to be established between the lens capsule and the IOL is determined. For example, the determination of the roll orientation can include determining an astigmatic axis of the eye and determining the roll orientation based at least in part upon the astigmatic axis of the eye. The anchoring capsulotomies of the pattern can be placed in locations configured to accomplish the determined roll orientation upon assembly of the IOL with the lens capsule. The roll orientation can be determined to correspond to a direction of natural asymmetry of contraction of the lens capsule.

In step 658, a confirmation that the IOL is at the determined roll orientation relative to the lens capsule is accomplished before coupling the IOL to the lens capsule. The roll orientation confirmation can be accomplished in any suitable manner. For example, the roll orientation confirmation can include observing a roll orientation of a keyed feature of the IOL. The roll orientation can include observing a roll orientation of a keyed feature of the lens capsule. The keyed feature of the IOL can be the relative positioning of the anchoring features. For example, in many embodiments, the pattern can be bisected along a bisecting angle to result in two symmetric pattern halves and the bisecting angle can be used as the keying feature. The keyed feature on the IOL can also be one or more keying markers created in the IOL. The keyed feature of the lens capsule can include one or more anatomic landmarks of the lens capsule. The keyed feature of the lens capsule can include one or more markers created in the lens capsule.

In step 660, the IOL is coupled to the lens capsule by mechanically engaging the anchoring features of the IOL with the pattern of anchoring capsulotomies in the lens capsule. When the IOL is coupled to the lens capsule it can be located, for example, in an anterior chamber of the eye, in a capsular bag of the eye, on the anterior side of a posterior capsule of the eye, or on the posterior side of the anterior capsule of the eye.

Although the above steps show method 650 in accordance with embodiments, a person of ordinary skill in the art will recognize many variations based on the teaching described herein. The steps may be completed in a different order. Steps may be added or deleted. Some of the steps may comprise sub-steps. Many of the steps may be repeated as often as if beneficial to the treatment.

One or more of the steps of the method 650 may be performed with the circuitry as described herein, for example one or more of the processor or logic circuitry such as the programmable array logic for field programmable gate array. The circuitry may be programmed to provide one or more of the steps of method 650, and the program may comprise program instructions stored on a computer readable memory or programmed steps of the logic circuitry such as the programmable array logic or the field programmable gate array, for example.

Methods 600, 610 and 650 can be combined in one or more of many ways, for example one or more steps of each method can be combined, and the combined steps may be completed in a different order, added or deleted, and some of the combined steps may comprise sub-steps, and may be implemented with the circuitry as described herein.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

What is claimed is:

1. A method for performing a laser-assisted treatment of an eye having a lens capsule, the method comprising:
    forming an anchoring capsulotomy in the lens capsule by using a laser to incise the lens capsule, the anchoring capsulotomy being configured to accommodate a drug eluting plug; and
    removably coupling the drug eluting plug to the anchoring capsulotomy, wherein the drug-eluting plug includes at least one cap on a body, wherein a portion of the body of the drug eluting plug is removably fitted through the anchoring capsulotomy to retain the drug eluting plug's position relative to the lens capsule, wherein the portion the body of the drug-eluting plug that passes through the anchoring capsulotomy includes pores configured for dispersion of a drug which is otherwise contained within the drug-eluting plug.

2. The method of claim 1, wherein the drug eluting plug is configured to time-release a drug or therapeutic agent, wherein the drug or therapeutic agent includes one or more of glaucoma medications, anti-vascular endothelial growth factor (VEGF) treatments, diclofenac sodium, ketorolac tromethamine, or cytotoxic LEC-specific genes.

3. The method of claim 1, further comprising:
    forming a central capsulotomy in the lens capsule by using the laser to incise the lens capsule,
    wherein the anchoring capsulotomy is adjacent to the central capsulotomy.

4. The method of claim 1, wherein the body of the drug-eluting plug has an end opposite the cap.

5. The method of claim 4, wherein the cap has an outer diameter of 0.5-4.0 mm and a thickness of 0.1-1.0 mm, the body has an outer diameter of 1.0-3.0 mm and a length of 1.0-3.0 mm, and the end has a radius of curvature of 0.125-4.0 mm.

6. The method of claim 1, wherein the body has a waist configured to engage within the anchoring capsulotomy.

7. The method of claim 1, wherein the anchoring capsulotomy has a buttonhole shape.

8. The method of claim 1, wherein the drug-eluting plug includes two caps located on two opposite ends of the body, the two caps being configured to retain the drug-eluting plug within the anchoring capsulotomy.

9. The method of claim 1, wherein the step of forming an anchoring capsulotomy includes forming a plurality of anchoring capsulotomies, wherein the anchoring capsulotomies are formed in an anterior capsule of the eye, or in a posterior capsule of the eye, or in both the anterior and posterior capsules.

\* \* \* \* \*